United States Patent
Moore et al.

(10) Patent No.: US 6,350,732 B1
(45) Date of Patent: *Feb. 26, 2002

(54) METHOD FOR EXTRACTING LIPIDS FROM TISSUE SAMPLES USING HIGH OSMOLALITY STORAGE MEDIUM AND PRODUCT

(75) Inventors: Mark A. Moore, Austin, TX (US); David T. Cheung, Arcadia, CA (US); Gerald L. Mechanic, deceased, late of Bellevue, WA (US), by Richard Mechanic, executor; Brian K. Mcilroy, Georgetown, TX (US)

(73) Assignee: Carbomedics, Inc., Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/971,273

(22) Filed: Nov. 17, 1997

Related U.S. Application Data

(63) Continuation-in-part of application No. 08/435,867, filed on May 4, 1995, now abandoned, which is a continuation-in-part of application No. 08/223,316, filed on Apr. 5, 1994, now abandoned, which is a continuation of application No. 07/893,314, filed on Jun. 3, 1992, now abandoned, which is a continuation-in-part of application No. 07/557,639, filed on Jul. 30, 1990, now Pat. No. 5,147,514, which is a continuation-in-part of application No. 07/388,003, filed on Aug. 2, 1987, now abandoned.

(51) Int. Cl.$^7$ ............................................. A61K 38/00
(52) U.S. Cl. ......................... 514/21; 530/356; 530/412
(58) Field of Search ....................... 204/157.5; 574/21; 530/356, 412

(56) References Cited

U.S. PATENT DOCUMENTS

| | | | |
|---|---|---|---|
| 3,152,976 A | 10/1964 | Kuntz | 204/158 |
| 4,448,770 A | 5/1984 | Epting, Jr. | 424/153 |
| 4,838,888 A | 6/1989 | Nashef | 623/2 |
| 4,874,606 A | 10/1989 | Boyle, et al. | 426/74 |
| 4,942,042 A | 7/1990 | Bhargava et al. | 424/683 |
| 5,028,437 A | 7/1991 | Jerrett | 424/535 |
| 5,098,960 A | 3/1992 | Frautschi | 525/359.3 |
| 5,126,135 A | 6/1992 | Yamada et al. | 424/401 |
| 5,147,514 A * | 9/1992 | Mechanic | 204/157.68 |
| 5,263,992 A | 11/1992 | Guire | 623/66 |
| 5,215,541 A | 6/1993 | Nashef et al. | 8/94.11 |
| 5,332,475 A | 7/1994 | Mechanic | 204/157.68 |
| 5,368,483 A | 11/1994 | Sutter et al. | 433/173 |
| 5,447,536 A | 9/1995 | Girardot et al. | 8/94.11 |
| 5,476,516 A | 12/1995 | Seifter et al. | 8/94.11 |
| 5,645,587 A | 7/1997 | Chanda et al. | 623/11 |
| 5,697,972 A | 12/1997 | Kim et al. | 623/2 |

OTHER PUBLICATIONS

Broom, N. D. "The Stress/Strain and Fatigue Behaviour of Glutaraldehyde Preserved Heart–Valve Tissue", J. Biomechanics, 1997, vol. 10, pp. 707–724.

Gendler, E., "Toxic Reactions Evoked by Glutaraldehyde–Fixed Pericardium and Cardiac Valve Tissue Bioprosthesis", Journal of Biomedical materials Research, vol. 18, 727–736 (1984).

Jorge–Herrero, E.,, et al., "Study of the Calcification of Bovine Pericardium:Analysis of the Implications of Lipids and Proteoglycans", Biomaterials, 1991, vol. 12, Sep.

Levy, R. J., et al., "Cardiovascular Implant Calcification:A Survey and Update", Biomaterials, 1991, vol. 12, Oct.

Girardot, M. N., et al., "Alpha–Aminoleic Acid, A New Compound, Prevents Calcification of Bioprostheticheart Valves", The 17th Annual Meeting of the Society for Biomaterials, May 1–5, 1991, p. 114.

Girardot, M. N., et al., "Development of the AOA Process as Antimineralization Treatment for Bioprosthetic Heart Valves", The 19th Annual Meeting of the Society for Biomaterials, Apr. 28–May 2, 1993, p. 266.

Girardot, M. N., et al., "Effect of AOA on Glutaraldehyde–Fixed Bioprosthetic Heart Valve Cusps and Walls: Binding and Calcification Studies", The International Journal of Artificial Organs, vol. 17, No. 2, 1994, pp. 76–82.

Girardot, M. N. et al., "Role of Glutaraldehyde in Calcification of Porcine Heart Valves: Comparing Cusp and Wall", Journal of Biomedical Materials Research, vol. 29, 1995, pp. 793–801.

Golomb, G., et al., "The Role of Glutaraldehyde–Induced Cross–Links in Calcification of Bovine Pericardium Used in Cardiac Valve Bioprostheses", AJP, Apr. 1987, vol., 127, No. 1, pp. 122–130.

Gott, J. P., et al., "Calcification of Porcine Valves: A Successful New Method of Antimineralization", Ann Thorac Surg, 1992, vol. 53, pp. 207–216.

Thubrikar, M. J., et al., "Role of Mechanical Stress in Calcification of Aortic Bioprosthetic valves", J Thorac Cardiovasc Surg, vol. 86, 1983, pp. 115–125.

Myers, D. J., et al., "Biocompatibility Testing of Stentless Heart Valves Treated With 2–Amino Oleic Acid, A New Antimineralization Agent", The International Journal of Artificial Organs, vol. 16, No. 6, 1993, p. 453.

Munro, M. S., et al., "Alkyl Substituted Polymers With Enhanced Albumin Affinity", Trans Am Soc Artif Intern Organs, 1981, vol. 27, 1981, pp. 499–503.

(List continued on next page.)

Primary Examiner—Elli Peselev
(74) Attorney, Agent, or Firm—Mark R. Wisner

(57) ABSTRACT

A method extracting lipids from tissue samples, particularly collagenous tissue samples for use in preserving the tissue samples, is disclosed. The product of the method of extracting the lipids is also disclosed. Extraction is accomplished by immersing the tissue sample in a medium which is an aqueous solution of a salt and a sugar that is buffered to maintain pH and which has a high (greater than about 4500 mosm) osmolality.

14 Claims, No Drawings

OTHER PUBLICATIONS

Moczar, M., et al., "Deterioration of Bioprosthetic Heart Valves", ASAIO Journal 1994, pp. M697–M701.

Magilligan, D. J., "The Future of Bioprosthetic Valves", Trans Am Soc Artif Intern Organs, vol. 34, 1988, pp. 1031–1032.

Levy, R. J., "Bioprosthetic Heart Valve Calcification:Clinical Features Pathobiology, and Prospects for Prevention", CRC Critical Reviews in Biocompatibility, vol. 2, Issue 2, pp. 147–187.

Thoma, R. J., "Poly(Ether)Urethane Reactivity With Metal–Ion in Calcification and Environmental Stress Cracking", Journal of Biomaterials Applications, vol. 1 Apr. 1987, pp. 449–486.

Goissis, G., et al., "The Chemical Protecting Group Concept Applied in Crosslinking of Natural Tissues With Glutaraldehyde Acetals", Artificial Organs, 22 (3), pp. 210–214.

Eberhart, R. C., "Surface Treatments to Improve the Albumin Affinity and Blood Compatibility of Polymers", Engineering in Medicine and Biology Magazine, Jun. 1989, pp. 26–29.

Parnis, S. M., "Acoustic Spectral Analysis of an Electrohydraulic Artificial Heart (TAH)", ASAIO Journal, vol. 41, No. 1, p. 9.

Wiebe, D., "Glutaraldehyde Release From Vascular Prostheses of Biologic Origin", Surgery (104), 1988, pp. 26–33.

Zilla, P., et al., "Improved Ultrastructural Preservation of Bioprostetic Tissue", J. Heart Valve Dis., vol. 6, No. 5, Sep. 1997, pp. 492–501.

Khor, E., "Methods for the Treatment of Collagenous Tissues for Bioprostheses", Biomaterials, 1997, vol. 18, No. 2, pp. 95–105.

Greene, T. W., et al., "Protection for the Carbonyl Group", Protective Groups in Organic Synthesis, pp. 175–223.

Cheung, D. T., et al., "Mechanism of Crosslinking of Proteins by Glutaraldehydeii. Reaction With Monomeric and Polymeric Collagen", Connective Tissue Research, 1982, vol. 10, pp. 201–216.

Nimni, M. E., "A Defect in the Intramolecular and Intermolecular Cross–Linking of Collagen Caused by Penicillamine", The Journal of Biological Chemistry, vol. 243, No. 7, Apr. 10, 1968, pp. 1458–1466.

Carpentier, A., et al., "Biological Factors Affecting Long–Term Results of Valvular Heterografts", Journal of Thoracic and Cardiovascular Surgery, vol. 58, No. 4, Oct., 1969, pp. 467–483.

Chvapil, M., et al., "Effect of Collagen Crosslinking on the Rate of Resorption of Implanted Collagen Tubing in Rabbits", vol. 11, 1977, pp. 297–314.

Nimni, M. F., et al., "Chemically Modified Collagen: A Natural Biomaterial for Tissue Replacement", Journal of Biomedical Materials Research, vol. 21, 1987, pp. 741–771.

Woodreof, F. A., "Use of Glutara.Ldehyde and Formaldehyde to Process Tissue Heart Valves", Processed Tissue Valves, vol. 2, pp. 1–9.

Schoen, F. J., et al., "Cuspal Components in Bioprosthetic Valve Calcification:Elucidation and Modification", Surgery for Heart Valve Disease, 1989, pp. 679–685.

Levy, R. J., et al., "Inhibition by Diphosphonate Compounds of Calcification of Porcine Bioprosthetic Heart Valve Cusps Implanted Subcutaneouslyin Rats", vol. 71, No. 2, Feb. 1985, pp. 349–356.

Webb, C. L., et al., "Al+++ Preincubation Inhibits Calcification of Bioprosthetic Heart Valve Tissue in the Rat Subdermal Model ", Trans Am Soc Artif Intern Organs, vol. 34, 1988, pp. 855–859.

Baldwin, M., et al., "Fe3+ Pretreatment Provides Sustained Inhibition of Bioprosthetic Heart Valve Calcifications", The 17th Annual Meeting of the Society for Biomaterials, May 1–5, 1991, p. 61.

Bernacca, G. M., et al., "Chemical Modification of Bovine Pericardium and its Effect on Calcification in the Rat Subdermal Model", Biomaterials, 1992, vol. 13, No. 6.

Chandra, J., "Prevention of Calcifications of Heart Valve Bioprostheses: An Experimental Study in Rat", Ann Thorac Surg, 1995, 60, S339–S324.

Vesely, I., et al., "The Hybrid Xenograph/Autograph Bioprosthetic Heart Valve: In Vivo Evaluation of Tissue Extraction", Ann Thorac Surg, 1995, 60, S359–S364.

Okoshi, T. et al., "A New Bioprosthetic Cardiac Valve With Reduced Calcification", ASAIO Transactions 1990, 36, pp. M411–M414.

Moore, M. A., et al., "Stabilization of Pericardial Tissue by Dye–Mediated Photooxidation", Journal of Biomedical Materials Research, vol. 28, 1994, pp. 611–618.

Oster, G., et al., "Dye Sensitized Photooxidation", J. Am. Chem. Soc. Oct. 5, 1959, vol. 81, pp. 5095–5099.

Cao, H., et al., "Characterization of Mechanical Properties of Photooxidation Modified Bovine Pericardium", 21st Annual Meeting of the Society for Biomaterials, Mar. 18–22, 1995, p. 82.

Rossi, et al., "Lipid Extraction Attenuates the Calcific Degeneration of Bovine Pericardium used in Cardiac Valve Bioprostheses", J. Exp. Path. (1990) 71, 187–196.

* cited by examiner

METHOD FOR EXTRACTING LIPIDS FROM TISSUE SAMPLES USING HIGH OSMOLALITY STORAGE MEDIUM AND PRODUCT

CROSS-REFERENCE TO RELATED APPLICATIONS

The present application is a continuation-in-part of application Ser. No. 08/435,867, filed May 4, 1995, entitled "Cross-Linking of Collagen Using High Osmolality Storage Medium," now abandoned. Ser. No. 08/435,867 was a continuation-in-part of Ser. No. 08/223,316, filed Apr. 5, 1994 and entitled "Photooxidative Cross-Linking of Collagen Using High Osmolality Storage Medium (as amended)," which application is now abandoned. Ser. No. 08/223,316 was a continuation of application Ser. No. 07/893,314, filed Jun. 3, 1992 and entitled "Storage Medium for Tissue Preservation," and which is now abandoned. Ser. No. 07/893,314 was itself a continuation-in-part of application Ser. No. 07/557,639, filed Jul. 30, 1990 and entitled "Process for Cross-Linking Collagenous Material and Resulting Product," now issued as U.S. Pat. No. 5,147,514. Ser. No. 07/557,639 was a continuation-in-part of application Ser. No. 07/388,003, filed on Aug. 2, 1987, now abandoned, and having the same title.

BACKGROUND OF THE INVENTION

The present invention relates to a method for extracting lipids from tissue samples for the purpose of storing and preserving the tissue samples and the product of that method. The method of the present invention is used to particular advantage as a storage solution prefatory to the cross-linking of the intact collagen fibrils of collagenous tissue samples. In more detail, the present invention relates to a high osmotic pressure (compared to physiologic) solution which has particular advantage when used as a storage medium for samples of collagenous tissue before cross-linking the collagen in the tissue with any number of methods including glutaraldehyde and/or in accordance with the method described in the above-referenced U.S. Pat. No. 5,147,514.

Photooxidative cross-linking of the collagen fibrils of tissue samples such as bovine pericardium in accordance with the method of U.S. Pat. No. 5,147,514 results in a product having physical and chemical properties which make that product particularly suitable for use as a biomaterial for use as an artificial tendon, heart valve, or pericardial patch. Such biomaterials are characterized by several properties which confer upon them significant advantages over previously available materials used as bioprosthetics. They are produced by harvesting a sample of such tissue, incubating the sample in an aqueous media solution of a photooxidative catalyst buffered to about physiological pH (6.8–8.6), and then irradiating with light to cross-link the collagen.

It was discovered that it was advantageous to "precondition" the tissue sample by incubation in a media solution which did not include the catalyst before transfer to the solution including the catalyst for irradiation. When preconditioned in this manner, the resulting product shows decreased susceptibility to proteolytic degradation. It was also discovered this high osmolality, first media solution not only gives desirable results when used to precondition the tissue sample before cross-linking by that photooxidative process but also when used to store the tissue sample before cross-linking with glutaraldehyde and other processes as known in the art. The method and product of the present invention appear to achieve this result by removing, or decreasing the content, of the non-collagenous components of the tissue sample, including, in particular, extracting lipids from the tissue sample. Because lipids, and particularly phospholipids, are the main component of the membranes of living cells, it appears that extraction of lipids has the desirable effect of devitalizing the tissue sample, thereby reducing the bioburden of the tissue sample. A reduction in bioburden is a strong indicator of a longer shelf life of the tissue sample, and for this reason, the high osmolality solution of the present invention is advantageously used as a storage medium for the collagenous tissue sample.

It has long been standard practice, for instance, in histological laboratories, to store tissue samples in alcohol at low temperature and to use freeze drying if the sample is to be preserved for longer periods of time. Standard practice for storage of samples for relatively short periods of time usually involves incubation in one of several known saline solutions, buffered to physiological pH, at low temperature. However, both methods jeopardize the maintenance of the native fibrillar structure of structural proteins such as collagen.

The maintenance of collagen fibrillar structure is of particular concern in light of experimental data indicating that the method described in U.S. Pat. No. 5,147,514 results in the cross-linking of the collagen fibrils in their true, native state, e.g., as intact collagen fibrils, and that this capability of that method appears to be responsible for the excellent mechanical properties of the resulting product and the ability of the product to resist in vivo degradation. It is, therefore, an object of the present invention to provide a process for extracting lipids from collagenous tissue samples before photooxidative cross-linking of the collagenous tissue sample. However, it is apparent from the results obtained when used in that process that the media solution and lipid extraction process of the present invention are useful in preserving tissues for other cross-linking processes, such as acyl azide, polyglycidylethers, carbodiimide, and glutaraldehyde cross-linking, and other cross-liking processes known in the art, for preservation of any proteinaceous material or tissue, and perhaps even more broadly, as a storage medium for many different types of tissues, biomaterials, and/or extracts or solutions of same and/or their component parts or molecules.

In a broad sense, therefore, it is an object of the present invention to provide a method for preserving biological specimens, tissues, extracts, biomolecules, and/or isolates which both maintains the native state of the sample and helps protect the sample from damage or degradation caused by harmful agents which may be found in the sample or opportunistic, invasive agents by extracting lipids from the sample.

It is another object to provide a method for lipid extraction having particular utility for storing tissue samples for longer periods of time than previously possible, e.g., for a period of several weeks, at room temperature.

Another object of the present invention is to provide a previously unknown product having decreased phospholipid content compared to fresh, or untreated, tissue samples, with a longer shelf life than previously possible.

These and other objects, as well as the several advantages of the invention, will be apparent to those skilled in the art upon reading the specification, the examples and the appended claims.

SUMMARY OF THE INVENTION

In accordance with the present invention, there is provided a method, or treatment, for extracting lipids from a collagenous tissue sample comprising immersing the sample in a high osmolality aqueous solution of a salt and a sugar, the salt being a salt selected from the group of salts which are capable of penetrating the sample, the sugar functioning to maintain the high osmolality of the solution even as salt concentration in the solution decreases as the salt penetrates the tissue sample, to decrease the bioburden of the sample as compared to the bioburden of untreated tissue samples. In a preferred embodiment, the salt and sugar are utilized in proportions in which the salt is utilized in a weight to volume ratio of higher than about 11.7% and the sugar is utilized in a concentration of about 30 to about 80% (W/V).

Also provided is a tissue sample having improved shelf life when maintained in an aqueous solution which is produced by immersing the tissue sample in a storage medium having an osmolality higher than about 4500 mosm, the storage medium comprising water, sucrose, and a halide salt, wherein the tissue sample is characterized by a decreased bioburden and a decreased lipid content relative to tissue samples which are not produced in this manner. In a preferred embodiment, the storage medium comprises about 30 to about 80% (W/V) sucrose, and the halide salt is utilized in a concentration of higher than about 11.7% (W/V).

DETAILED DESCRIPTION OF THE INVENTION

Once removed from the animal, collagenous tissue can become hydrated and thicken. The thickening of the tissue is believed to be the result of the partial unwinding of the collagen fibrils, which makes the fibrils more susceptible to enzymatic degradation. The interaction of native helical collagen molecules inside the collagen fibrils must be kept intact in order to maintain the stability of the fibrils. To do so, it has been discovered that the ionic strength of the solution in which the sample is stored must be increased to such a point that the hydrophobic interaction between collagen molecules is maximized. This is accomplished by the use of a high salt concentration in the media solution of the present invention.

However, as the salt in the solution penetrates the tissue sample, and depending upon diffusion time across the thickness of the tissue and the actual thickness of the tissue, it is believed that a concentration gradient is set up between tissue and solution. As the salt concentration in the tissue increases to about one molar at physiological pH, the ionic interaction between collagen molecules in the fibril is interrupted by interaction between the collagen molecules and the salt, resulting in the unwinding of the fibril and subsequent solubilization of the fibril. It is therefore believed that the high concentration of sugar in the media solution of the present invention maintains the osmolality of the solution and serves as a component to cause the short term aggregation of the collagen fibrils. The osmolality (represented by the Greek letter $\mu$) of the storage medium of the present invention is preferably higher than the osmolality of 3.0 M NaCl solution, e.g., 4500 mosm, and in a presently preferred embodiment, the osmolality is higher than about 6000 mosm. The upper limit of the osmolality is imposed by the practicalities of handling the solution, e.g., the increasing viscosity that results from high solute content. Of course, the osmolality is also limited by the ability of the solvent to hold solute, e.g., the point at which it is saturated. Both sugar and salt contribute to the osmolality of the medium of the present invention (as compared to the ionic strength of the solution, which results from inclusion of the salt, which dissociates in water) and the relative contributions of salt and sugar to the osmolality of the solution are not as important to the function of the solution as the total osmolality. Maintenance of the high osmolality of the solution in the face of depletion of the concentration of the salt by penetration into the tissue appears to mitigate collagen denaturation by maintaining the hydrophobic interaction of the collagen fibrils in the same manner as the salt functions to maintain collagen aggregation.

Many salts are suitable for use in the storage medium of the present invention, but those which will function as described above to penetrate a tissue sample to inhibit hydration of the proteinaceous material in its native configuration are specifically contemplated. Due to their low cost, high solubility, and ready availability, sodium chloride and potassium chloride are the preferred salts for use as the salt in the storage medium of the present invention, and consequently, the examples set out below refer to those salts. However, many other such salts are readily known in the art and readily available, including, for instance, the ammonium, sodium, calcium, magnesium, manganese, and potassium salts of halides, nitrites, nitrates, phosphites, phosphates, sulfites, sulfates, and alkanoic acids such as propionates, acetates, and formates, and specifically, the aforementioned sodium and potassium chloride, magnesium chloride, and sodium nitrite. All such salts, as well as the many which are not listed here but which would be recognized by those skilled in the art who have the benefit of this disclosure to function in substantially the same way to achieve substantially the same result as those which are listed, are contemplated by the present invention.

As a general guideline, the desired contribution to the osmolality of the storage medium of the present invention attributable to the salt component is achieved by inclusion of, in the case of NaCl, about 2.0 to about 5.0 M NaCl in the medium (e.g., from about 116.8 to about 284.0 g per kilogram (e.g., one liter) final volume of water, or about 11.7 to about 28.4% (W:V) concentration), the preferred range being about 2.25–4.0 M. For salts such as calcium chloride, the desired contribution to the osmolality of the medium is achieved by inclusion of from about 1.3 to about 3.4 M $CaCl_2$ in the medium, and so on.

Similarly, many sugars can be used as the second component of the storage medium of the present invention. Again because of its low cost, high solubility, and ready availability, most of the examples set out below refer to the use of sucrose as the sugar in the storage medium. However, those skilled in the art will recognize that other sugars such as glucose, fructose, mannose, galactose and any other monosaccharides, disaccharides such as maltose, cellobiose, and lactose, trisaccharides, or polysaccharides such as amylose or amylopectin, as well as sugar derivatives such as sorbitol (derived from glucose by reduction of the aldehyde group), mannitol, etc., glycosides such as methyl glucoside (derived from glucose by acid-catalyzed reaction of methanol with glucose), or proteoglycans will also function in substantially the same way to achieve the desired result of maintaining the proteineous materials of a tissue sample in their native state, and all such sugars are contemplated as falling within the scope of the present invention.

In the case of sucrose, the desired contribution to the osmolality of the storage medium of the present invention can generally be obtained by using a concentration of from about 30 to about 85% W:V (e.g., from about 0.3 to about 0.85 kg per kg, e.g., one liter, final volume of water) sucrose, the preferred range being from about 30 to about 80% W:V concentration, e.g., about 0.85 to about 2.35 M sucrose. In other words, the contribution of the sugar to the total osmolality of the storage medium of the present invention ranges from about 3400 mosm upwardly to the saturation point of the solvent.

In some salts which are not as soluble as others, the desired contribution to the osmolality of the media is obtained by increasing the amount of sugar in the solution. By compensating for solubility in this manner, satisfactory results are obtained even with certain salts such as potassium chloride, potassium iodide, sodium citrate, sodium acetate, and sodium sulfate. These salts are listed here because it was discovered that, at least when the media of the present invention is made by the following method, they were not completely solublized. This method, which is but one way to prepare the media and is described here to better illustrate the teaching set out above as to the upper limits on the concentration of the salt imposed by the practicalities of dissolving one or both of the components of the solution, was an attempt to prepare the solution of the present invention using various salts and a standard of 67 g of sucrose per 100 ml final volume. Because sugar occupies a large volume, the first step was to attempt to dissolve 0.3 moles of various salts in 40 ml PBS by overnight stirring at room temperature. If soluble, then the 67 g sucrose was added (again by stirring overnight at room temperature) and the final volume adjusted 100 ml with PBS to prepare the 3 M salt and 67% W:V sucrose solution that was desired. The combinations of salts and sucrose were as follows:

| SALT | WEIGHT | ADD 40 ml PBS | SOLUBLE? | pH | ADD 67 g SUCROSE | SOLUBLE? |
|---|---|---|---|---|---|---|
| Magnesium chloride | 61.0 g | √ | YES | 3.15 | √ | YES |
| Potassium chloride | 22.4 g | √ | NO | N/A | N/A | N/A |
| Potassium Iodide | 49.8 g | √ | NO | N/A | N/A | N/A |
| Manganese sulfate | 45.3 g | √ | YES | 0.54 | √ | NO |
| Sodium citrate | 88.2 g | √ | NO | N/A | N/A | N/A |
| Sodium acetate | 24.6 g | √ | NO | N/A | N/A | N/A |
| Sodium phosphate (mono- and dibasic-, equimolar) | 20.7 g 21.3 g | √ | YES | 5.75 | √ | NO |
| Sodium nitrite | 20.7 g | √ | YES | 6.52 | √ | YES |
| Sodium sulfite | 42.6 g | √ | NO | N/A | N/A | N/A |

The weights of each salt added were calculated for a total of 0.3 moles of salt to be added for each solution and take into account the total molecular weight of the salt as provided in the anhydrous or hydrated form (N/A=not applicable).

In a second set of experiments, the media for use in accordance with the improved method of the present invention was prepared using a standard of 17.5 g sodium chloride along with 67 g of various sugars per 100 ml final volume. Because the sugar occupies a large portion of the volume, the first step was to dissolve the 17.5 g of sodium chloride in 40 ml PBS then 67 g of the particular sugar was added. The final volume was adjusted to 100 ml with PBS to prepare the 3 M salt and 67% W:V sucrose solution that was desired.

The fructose was not completely soluble in the total volume of 100 ml. Therefore, an additional 33 ml PBS was added to solublize all of the components. Thus, this solution was 50% fructose and 2.25 M NaCl. It will be understood by those skilled in the art who have the benefit of this disclosure that those solutions which were not able to be prepared by these methods may be prepared by other methods known in the art and that even a solution such as the sodium chloride-fructose solution, in which additional PBS was added to solublize the fructose, gave satisfactory results (as set out below) when used in accordance with the present invention.

Although the examples set out above disclose a number of high osmolality solutions which are used to advantage in the method of the present invention, there are many other such solutions which may also be utilized to advantage, including solutions which are comprised of the very salts and/or sugars listed above as being insoluble by the method described in those examples. Those skilled in the art who have the benefit of this disclosure will recognize that additional solute can be solublized by using, for instance, elevated temperature, more efficient and more vigorous stirring and/or agitation, and by other methods known in the art.

It will also be recognized that some salts cause a decrease in pH when dissolved (note the pH of the above-described solutions including manganese sulfate and magnesium chloride). Further, this lowering of pH can have detrimental effect(s) on the collagenous tissue to be cross-linked. Reference is made, for instance, to Example 4, infra, wherein it is reported that a solution made in accordance with the present invention and comprised of magnesium chloride and sucrose had a pH of 3.59. When that tissue was evaluated by heat shrink test, there was no sharp decrease in tissue length as a function of temperature, indicating that the tissue was likely damaged by this low pH. Even so, the magnesium chloride/sucrose solution can be used to advantage in connection with the present invention by, for instance, neutral-

| SALT | WEIGHT | ADD 40 ml PBS | SOLUBLE ? | SUGAR TO ADD | ADD 67 g SUGAR | SOLUBLE? |
|---|---|---|---|---|---|---|
| Sodium chloride | 17.5 g | √ | YES | Amylose | √ | NO |
| Sodium chloride | 17.5 g | √ | YES | Glucose | √ | NO |
| Sodium chloride | 17.5 g | √ | YES | Lactose | √ | NO |
| Sodium chloride | 17.5 g | √ | YES | Fructose | √ | YES |
| Sodium chloride | 17.5 g | √ | YES | Sucrose | √ | YES | izing the acidity of the solution by addition of sufficient magnesium hydroxide to raise the pH or by using a stronger butter. Such adjustments in pH are known to those skilled in the art and the resulting solution gives satisfactory results when used in the method of the present invention.

The storage medium is buffered to physiological pH by use of any of a number of commonly used buffers, one of the most commonly available being phosphate buffered saline (PBS), and that buffer is used to advantage in the medium of the present invention. Other suitable buffers include those containing potassium or sodium phosphate, or potassium or sodium chloride, such as a Good's buffer, e.g., HEPES, TES, or BES (Research Organics, Inc.), preferably at concentrations of from about 0.2 to about 1.0 M. However, the molar concentration of the buffer is not as important as the concentration of the other two components of the storage solution of the present invention. Almost any concentration of buffer components which will maintain pH between about 3.5 and about 10, and preferably at about physiological pH, will function effectively in connection with the storage medium of the present invention. By reference to the term "physiological pH" herein, it is intended to refer to nominal hydrogen ion concentration in vivo; those skilled in the art will recognize, and the term is specifically intended to encompass, that a pH range of from about 6.8 to about 8.6 may be encountered, depending upon the system, in normal living systems.

The following non-limiting examples describe the invention in further detail.

EXAMPLE 1

A rectangular illumination cell was constructed from clear plastic with an outer jacket of the same material and tubes communicating with the inner chamber for circulation of media and dye. A frame, comprised of narrow strips of plastic including spaced holes therealong for suturing tissue sample thereto, was constructed in a size fitting into the inner chamber of the cell. After suturing a piece of bovine pericardium to that frame and inserting the frame into the inner chamber, a media comprised of 2.8 M potassium chloride, $\mu$=0.164, potassium phosphate buffer, pH 7.4, including 50% W:V sucrose, was circulated through the inner chamber of the illumination cell. After soaking in this high osmotic pressure media, the tissue was incubated in media including 0.02 M sodium phosphate buffer, pH 7.4, containing 0.01% (wt/vol) methylene green and illuminated for 24 and 48 hours by two 150 watt flood lamps at a distance of about 4.5 cm while holding temperature at between −2° C. and 6° C.

After irradiation, small pieces of tissue from each sample were digested with pepsin (1% pepsin solution in 3% acetic acid at 4° C. for 24 hrs.) or bacterial collagenase (1% collagenase solution in 0.15 TES buffer, pH 7.5, in 0.01 M $CaCl_2$ at 37° C. for 6 hrs.). The following ratios of hyp/mg of tissue in the enzyme columns clearly demonstrate the cross-linking of the tissue samples (the control samples were not illuminated).

| Time of Irradiation (hrs.) | Pepsin | Collagenase |
|---|---|---|
| 0 (Control #1) | 26 | 314 |
| (Control #2) | 31 | 314 |
| 24 (Sample #1) | 0 | 410 |
| (Sample #2) | 0 | 290 |
| 48 | 0 | 303 |

Additional tissue samples were further stabilized (without apparent change in their tactile properties, e.g., tissue texture and suppleness) by reduction of the newly formed iminium bonds by immersion in a solution of $NaBH_4$ for one hour as demonstrated by the following hyp/mg ratios:

| Time of Irradiation (hrs.) | Pepsin | Collagenase |
|---|---|---|
| 0 (Control #1) | 26 | 314 |
| (Control #2) | 7 | 208 |
| 24 (Sample #1) | 0 | 180 |
| (Sample #2) | 0 | 170 |
| 48 | 0 | 170 |

EXAMPLE 2

Soluble BAPN rat type I collagen in 0.5 M HAc was divided into six 4 ml samples and each sample placed in a dialysis bag with 300 mg NaCl (no salt was added to sample 5 and 6). Samples were dialyzed into the high osmotic strength buffer described in Example 1 (samples 5 and 6 were dialyzed into phosphate buffered saline (PBS), pH 7.4) and 2 ml of 0.2% methylene blue. Samples 2 and 3 were transferred to buffer including 0.1% methylene blue in PBS, sample 4 was transferred to PBS including 0.1% methylene blue, and samples 5 and 6 remained in PBS. Sample 2 was exposed to a 150 watt white floodlight located about 7 inches from the surface of the fluid while holding temperature between about 8 and 12° C. for eight hours, samples 3 and 4 were exposed for 24 hours under the same conditions, and samples 5 and 6 were exposed for two hours under the same conditions. All samples were then dialyzed back into HAc until the solutions were no longer blue and then analyzed by SDS-PAGE. The samples exposed for 24 hours were more cross-linked than those exposed for eight hours, and all samples were more cross-linked than samples 5 and 6.

EXAMPLE 3

Bovine pericardial tissues were harvested from a local abattoir and stored in plastic ZIP LOCK® bags on ice until cleaned. Residual fat was removed from each tissue and the tissues maintained on wet ice with minimal fluid contact until immersed in the appropriate storage solution (each buffered with 0.13 M sodium chloride-phosphate buffered saline).

| Solution | Salt | Sucrose (W:V) |
|---|---|---|
| 1 | 2.5 M | 50% |
| 2 | 3.0 M | 60% |
| 3 | 4.0 M | 67% |
| 4 | 2.5 M | 67% |
| 5 | 4.0 M | 50% |
| 6 | PBS control (pH 7.4, 300 mosm) | |

Tissues preserved in solutions 1–5 were stored at room temperature; the PBS (solution 6) was presterilized by filtration through 0.2 micron filters. Tissue preserved in PBS (solution 6) was stored at 4° C.

Samples were removed from each solution at time periods of 1, 7, 28, and 56 days, washed free of the storage solution with freshly prepared, sterile PBS for 2 hrs., and aerobic bioburden was measured using the method described at U.S. Pharmacopeia XXII, The U.S.P. Convention, Inc.; Rockville, Md., pp. 1481–2 (1990). The results are set out below as average total recoverable aerobic bioburden, in CFU's per sample, for two specimens:

|          | Preservation Time (Days) | | | | |
| -------- | ---- | ----- | ------ | ------ | --------- |
| Solution | 0    | 1     | 7      | 28     | 56        |
| 1        | 3643 | 760   | 1700   | 8130   | 22.5      |
| 2        | 2400 | 363   | 68     | 43     | 2958      |
| 3        | 7455 | 308   | 220    | 80     | 65,425    |
| 4        | 2665 | 245   | 100    | 365    | 19,700    |
| 5        | 4378 | 3375  | 313    | 9355   | 74,200    |
| 6        | 1610 | 9175  | 12,053 | 10,983 | 7,785,000 |

These data suggest that solutions 1–5 had a significant effect on the bioburden levels of the tissue. The bioburden level of the tissue stored in PBS (solution 6) increased dramatically after one day to an approximately constant level for 28 days whereas the microbial levels of tissue stored in solutions 1–5 all decreased after one day of storage. After one week of storage, the bioburden levels were significantly lower than at harvest (T=0). At 28 days, the bioburden levels or solutions 1 and 5 (50% sucrose) were comparable to the levels of tissue stored in PBS (solution 6), but tissues maintained microbial levels of less than 500 CFU/sample. At 56 days, the microbial levels for all solutions except solution 1 were significantly increased compared to the 28 day specimens, but these levels were still 100-fold less than that of PBS-stored tissue.

EXAMPLE 4

Bovine pericardial tissue was received on ice from the abattor on the day after harvest. Separate bioburden analysis of the tissue received in this shipment indicated:

aerobic count=$3.6 \times 10^3$ cfu (colony forming units)/g tissue
aerobic spore formers<10 cfu/g
fungal count=30 cfu/g.

Twenty-five pieces approximately ¾"×1" were cut from a sac and five each were placed in 50 ml each of the following solutions:

1. phosphate buffered saline (PBS), pH 7.3–7.4
2. sucrose, magnesium chloride media
3. sucrose, sodium nitrite media
4. fructose, sodium chloride media
5. sucrose, sodium chloride media.

Solutions 2–5 were made by dissolving 0.3 moles salt in 40 ml PBS, adding 67 g sugar, and adjusting final volume to 100 ml with PBS to give a 3 M salt, 67% W:V sugar solution in accordance with the present invention. The fructose was not completely soluble in the total volume of 100 ml. An additional 33 ml of PBS was added to give a solution that was 50% fructose and 2.25 M NaCl. The salt added was calculated as the weight of the salt as provided in the anhydrous or hydrated form, for a total of 0.3 moles of salt for each solution.

After samples were stored in solution at room temperature for 12 days, one piece of tissue and 10 ml of each solution were analyzed for bioburden and two pieces of tissue were removed from each sample container and placed in a 50 ml volume of 0.5% glutaraldehyde in PBS, maintained for two days, split lengthwise and analyzed by shrinkage temperature analysis. Shrinkage temperature is a measure of thermal stability and is known to rise upon fixation by glutaraldehyde (C. A. Pereira, et al., "Effect of alternative crosslinking methods on the low strain rate viscoelastic properties of bovine pericardial bioprosthetic material," 24 J. Biomed. Mater. Res. 345–361 (1990)). To perform this test, a piece of tissue was mounted on two extensometers, placed in a water bath, and the temperature was slowly raised. The length of the tissue was monitored as a function of temperature. When the tissue reached its shrinkage temperature there was a very rapid decrease in length. The temperature at the maximal rate of tissue shortening was taken as the shrinkage temperature. Values reported are an average of two separate measurements. The data are summarized below.

| Solution (NOTE: pH of solutions were taken upon completion of experiment) | Tissue bioburden* Aerobic count (cfu/g) | Liquid bioburden# Aerobic count (cfu/ml) | Shrink temperature- tissue from solutions (° C.) | Shrink temperature- tissue from glutaraldehyde (° C.) |
| --- | --- | --- | --- | --- |
| PBS | $1.2 \times 10^5$ | $2.6 \times 10^6$ | 67.1 | 83.7 |
| Sucrose, Magnesium chloride, pH 3.59 | <10 | 2 | not measurable† | not measurable† |
| Sucrose, Sodium nitrite, pH 7.38 | 20 | 1 | 65.6 | 77.2 |
| Fructose, Sodium chloride, pH 5.73 | <10 | 0 | 66.3 | 82.5 |
| Sucrose, Sodium chloride, pH 6.01 | <10 | 2 | 66.0 | 83.5 |

*Aerobic spore formers and fungal counts were <10 cfu/g for all 5 tissue samples.
Aerobic spore formers and fungal counts were 0 cfu/ml for all 5 solutions.
†A shrinkage temperature could not be evaluated for tissue which had been stored in the sucrose/magnesium chloride solution, with or without subsequent glutaraldehyde treatment. Allthough the tissue did shrink, there was no sharp decrease in tissue length as a function of temperature, indicating that the tissue was likely damaged.
§Pericardial tissue which was freshly received was used as a control and gave a shrinkage temperature of 65.4° C.

EXAMPLE 5

Having found in Examples 3 and 4 that the bioburden of collagenous tissue samples was decreased by storing in the high osmolality solution of the present invention, a series of experiments was conducted in an attempt to determine the cause of that beneficial result. A series of porcine aortic valve and bovine pericardial samples, harvested from a local abbatoir in the manner described in Example 3, were tested to determine their protein and lipid phosphorous contents before and after storage in the high osmolality solution of the present invention. After storage in the high osmolality storage solution of the present invention for time periods ranging between 7 and 21 days, the tissue samples were extracted in a 3:2 mixture of hexane:isopropanol (V:V) and analyzed for lipid phosphorous content by the method described in E. Gottfried, 8 J. Lipid Res. 321–327 (1967), which article is hereby incorporated into this specification as if fully set forth herein by this specific reference. Briefly, that method involved digesting the sample in 70% perchloric acid at 180° C. for two hours and complexing with ammonium molybdate (25%) at 100° C. for five minutes in the presence of 10% ascorbic acid. Absorbance was then assayed spectrophotometrically at 797 nm to determine lipid phosphorous concentration.

Samples A–H (see below) were prepared from porcine aortic valves; samples HP and HS were prepared from bovine pericardium. Each sample was placed in either HSHS solution of the present invention set out in Example 3, above, as Solution 4 or prior art preservatives in accordance with the following schedule:

A Not stored in HSHS (Control)
B Immersed in 10% HSHS for 1–2 days, 20% HSHS for 1–2 days, 30% HSHS for 1–2 days, 50% HSHS for 1–2 days, and then stored in 100% HSHS
C Immersed in 10% HSHS for 1 day, 20% HSHS for 1 day, 30% HSHS for ½ day, 50% HSHS for 2 days, and then stored in 100% HSHS
D Immersed in 10% ethanol for 1 day, 20% ethanol for ½ day, 30% ethanol for 2 days, 40% ethanol for ½ day, and then stored in 50% ethanol
E Immersed in 10% glycerol for ½ day, 20% glycerol for 1 day, 30% glycerol for 2 days, 40% glycerol for ½ day, 50% glycerol for 1 day, 75% glycerol for 1 day, and then stored in 100% glycerol
F Immersed in 1% SDS for 1 day and then stored in 100% HSHS
G Immersed and stored in 100% HSHS
FP Not stored in HSHS (Control)
HP Immersed and stored in 100% HSHS The results are presented in tabular form as follows:

| | Sample | Phosphorous | % Drop From Fresh |
|---|---|---|---|
| A | Fresh | 5.15 ± 0.68 | — |
| B | HSHS Slow Graded Rinse | 1.79 ± 0.20 | 65% |
| C | HSHS Quick Graded Rinse | 0.88 ± 0.23 | 83% |
| D | EtOH Graded Rinse | 3.09 ± 0.52 | 40% |
| E | CCl$_3$/MetOH Rinse | 0.22 ± 0.06 | 49% |
| F | Glycerol Graded Rinse | 1.56 ± 0.1 | 70% |
| G | SDS Rinse | 5.13 ± 0.74 | 0.3% |
| H | HSHS Valve | 0.30 ± 0.05** | 94% |
| FP | Fresh Pericardium | 0.30 ± 0.07 | — |
| HP | HSHS Pericardium | 0.01 ± 0.001** | 97%* |

**These were analyzed on a different date and there where multiple extra rinses conducted on these samples prior to analysis. The HSHS presented problems at the testing lab for these samples.

The data set out in the preceeding table is presented in nmole/mg tissue (dry weight) and each result represents the average of three replications. Percentage reduction from 5.15±0.68 of fresh (control) tissue was greater than (a) 2σ (standard error) different than the control and (b) all significantly different by Student's t test with 95% confidence for samples B, C, D, E, F, H and HP.

It is noted, however, that the lipid phosphorous content in normal (control) tissue samples ranged from 4.35 to 6.00 nmoles/mg tissue (dry weight) and that the "percentage reduction from fresh" set out in the last column of the preceeding table was calculated from the average of the three samples which were tested fresh, e.g., without processing. Reports in the literature indicate that the lipid phosphorous content of various collagenous tissues ranges from 0.5–20.6 nmole/mg tissue, and those skilled in the art will recognize from this information that the percentage reduction in lipid phosphorous content resulting from extraction by the method of the present invention depends on the pre-processing lipid phosphorous content of the sample and a number of other factors. These other factors may include, for instance, the cleanliness of the conditions under which the sample was harvested, the speed with which the sample is immersed in ice, the number of rinses of the sample before being assayed, the type of tissue, the type of rinse, and other factors too numerous to mention here. Because of these many factors, those skilled in the art will recognize from these data that percentage reduction is set out in the preceeding table as a statistical aid to help interpret the results set out in the table and that this information is not intended to infer that the method of the present invention must extract a certain minimum percentage of the lipids of the sample in order to function for its intended purpose, i.e., increasing the shelf life by decreasing the bioburden of the sample.

EXAMPLE 6

Of course it is also important that the method of the present invention result in a product which is stabilized against further chemical and/or enzymatic degradation. To assess the stability of the product of the present invention, assays for extractable protein and enzyme (pepsin) digestion were conducted on various samples of collagenous tissue which were stored for various times in the HSHS storage medium for various times. These tissue samples were bovine pericardium and bovine carotid arteries, harvested fresh in the manner described above in connection with Example 5, porcine valve leaflets, and porcine valve walls.

The extraction assay measures extractable protein and is conducted in the manner described in M. A. Moore, et al., 28 J. Biomed. Materials Res. 611–618 (1994), which reference is incorporated herein in its entirety by this specific reference thereto. Briefly, that method involves exposing the tissue sample to harsh solvent conditions and then analyzing the eluent for extracted proteins by polyacrylamide gel electrophoresis (PAGE). An increase in eluted proteins over time indicates degradation of tissue. The results are set out in tabular form as follows:

| Tissue Type | Extraction Assay | Enzyme Digestion |
|---|---|---|
| Bovine Pericardium | No changes in protein extraction pattern after HSHS storage for up to 3 months | No changes in pepsin digestion patters after storage up to 3 months |
| Bovine Carotid Arteries | Loss of lower M.W. bands after storage in HSHS for up to 2 months | No changes in pepsin digestion patters after storage up to 2 months |
| Porcine Leaflets | No changes in protein extraction pattern after HSHS storage for up to 5 months | No changes in pepsin digestion patters after storage up to 5 months |
| Porcine Walls | No changes in protein extraction pattern after HSHS storage for up to 5 months | No changes in pepsin digestion patterns after storage up to 5 months |

Three of the tissue types (bovine pericardium, porcine valve leaflets, and porcine valve walls) showed no significant difference in the extraction elution pattern after storage for up to 3–5 months. This result indicates that no significant degradation of the tissue occurred over this length of time. The other tissue sample, bovine carotid arteries, also showed no significant change in elution profile in the region of intact collagen and most other elutable proteins. However, there was a dramatic decrease in elutables over time over the two month storage time in a lower molecular weight region which may have been due to extraction of membrane lipids. Histological observation of various tissue samples was consistent with these results.

The pepsin digestion assay measures stability of tissue to proteolytic digestion and is an indicator of in vivo stability of the tissue. Thus, tissue which has been degraded or denatured is more susceptible to pepsin digestion. This assay was also conducted in accordance with the method set out in M. A. Moore, et al., supra. Briefly, tissue is exposed to a pepsin solution and the eluent is analyzed for released proteins by PAGE. An increase in eluted proteins is indicative of degradation or denaturation of the proteinaceous components of the tissue sample. The results are also set out in the above table, and all of the tissue types assayed showed no significant difference in the elution pattern after storage for up to 2–5 months and following pepsin exposure. These results indicate that no significant degradation of the tissue occurred in this time frame.

While the present invention has been described in detail for purposes of clarity and understanding, it will be clear to one skilled in the art from a reading of the disclosure that changes can be made in form and detail without departing from the true scope of the invention.

What is claimed is:

1. A treatment for extracting lipids from a collagenous tissue sample comprising immersing the tissue sample in an aqueous solution of a salt and a sugar, the salt being selected from the group of salts which are capable of penetrating the sample, the sugar functioning to maintain the osmolality of the solution higher than about 4500 mosm even as the salt concentration in the solution decreases as the salt penetrates the sample.

2. The treatment of claim 1 wherein said salt is utilized in a weight to volume ratio of higher than about 11.7% and said sugar is utilized in a concentration of about 30 to about 80% (W/V).

3. The treatment of claim 1 wherein said salt is either sodium chloride or potassium chloride.

4. The treatment of claim 1 wherein said sugar is either sucrose or fructose.

5. The treatment of claim 1 additionally comprising maintaining the osmolality of the solution at higher than about 4500 mosm.

6. The treatment of claim 1 wherein said salt is a halide salt.

7. A tissue sample having at least a 65% lower lipid content relative to fresh tissue samples produced by the method of claim 1.

8. A method for extracting lipids from a collagenous tissue sample for the purpose of preserving the sample comprising the steps of immersing a collagenous tissue sample in an aqueous medium and maintaining the osmolality of the medium in which the sample is immersed higher than about 4500 mosm, the storage medium comprising water, about 30 to about 80% (W:V) sucrose, and a halide salt in a concentration of higher than about 11.7% (W:V).

9. The method of claim 8 wherein said halide salt is either sodium chloride or potassium chloride.

10. The method of claim 9 wherein said medium additionally comprises a buffer.

11. A tissue sample having at least a 65% lower lipid content than fresh tissue samples produced by the method of claim 8.

12. A product obtained by immersing a collagenous tissue sample in an aqueous medium comprising water, sucrose, and a halide salt and maintaining the osmolality of the medium at higher than about 4500 mosm and characterized by the properties of having a lipid content at least 65% lower than fresh tissue samples and a lower bioburden than fresh tissue samples.

13. The product of claim 12 wherein the medium comprises about 30 to about 80% (W:V) sucrose and a halide salt in a concentration of higher than about 11.7% (W:V).

14. The product of claim 13 wherein the medium additionally comprises a buffer.

* * * * *